US010702652B2

(12) United States Patent
Teach

(10) Patent No.: US 10,702,652 B2
(45) Date of Patent: Jul. 7, 2020

(54) INJECTION DEVICE

(71) Applicant: Adam Teach, Williamsville, NY (US)

(72) Inventor: Adam Teach, Williamsville, NY (US)

( * ) Notice: Subject to any disclaimer, the term of this patent is extended or adjusted under 35 U.S.C. 154(b) by 289 days.

(21) Appl. No.: 15/812,147

(22) Filed: Nov. 14, 2017

(65) Prior Publication Data

US 2018/0133402 A1 May 17, 2018

Related U.S. Application Data

(60) Provisional application No. 62/422,206, filed on Nov. 15, 2016.

(51) Int. Cl.
| | | |
|---|---|---|
| *A61M 5/00* | (2006.01) | |
| *A61M 5/20* | (2006.01) | |
| *A61M 5/315* | (2006.01) | |
| *A61M 5/24* | (2006.01) | |
| *A61M 5/32* | (2006.01) | |

(52) U.S. Cl.
CPC ........ *A61M 5/2033* (2013.01); *A61M 5/2422* (2013.01); *A61M 5/31505* (2013.01); *A61M 5/3202* (2013.01); *A61M 2005/206* (2013.01); *A61M 2005/2013* (2013.01); *A61M 2005/2407* (2013.01); *A61M 2207/00* (2013.01)

(58) Field of Classification Search
CPC ................ A61M 2005/2013; A61M 2005/208
See application file for complete search history.

(56) References Cited

U.S. PATENT DOCUMENTS

| | | | | |
|---|---|---|---|---|
| 8,246,588 | B2* | 8/2012 | Gyrn | A61M 5/158 |
| | | | | 604/164.08 |
| 9,358,346 | B2* | 6/2016 | Fabian | A61M 5/34 |
| 9,724,472 | B2* | 8/2017 | Hourmand | A61M 5/2033 |
| 10,179,211 | B2* | 1/2019 | Rozwadowski . | A61B 5/150183 |
| 2009/0318864 | A1* | 12/2009 | Carrel | A61M 5/326 |
| | | | | 604/117 |
| 2010/0312195 | A1* | 12/2010 | Johansen | A61M 5/2033 |
| | | | | 604/192 |
| 2014/0207077 | A1* | 7/2014 | Iwase | A61M 5/32 |
| | | | | 604/198 |
| 2017/0106146 | A1* | 4/2017 | Folk | A61M 5/20 |
| 2018/0353693 | A1* | 12/2018 | Wendland | A61M 5/3204 |

* cited by examiner

*Primary Examiner* — William R Carpenter
(74) *Attorney, Agent, or Firm* — Stadler IP Law PLLC

(57) ABSTRACT

An injection device is provided having a housing with a plunger stop block and a cartridge assembly for holding a fluid. The cartridge assembly has a plunger that has an injection needle. A main spring assembly having a main spring and a plate having first and second support arms is positioned in the housing. A release component is positioned in the housing and includes a release ring having teeth with sliding surfaces, and the release ring defines first and second release slots. An actuator having an actuator ring from which actuator rods extend is positioned in the housing. The actuator rods can engage the sliding surfaces of the teeth, such that when a force is applied to the actuator ring the release component rotates and releases the main spring, and this causes the plunger to contact the plunger stop block and drive fluid out of the injection needle.

14 Claims, 7 Drawing Sheets

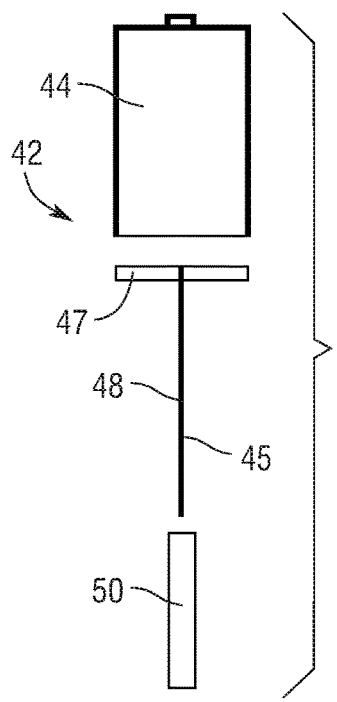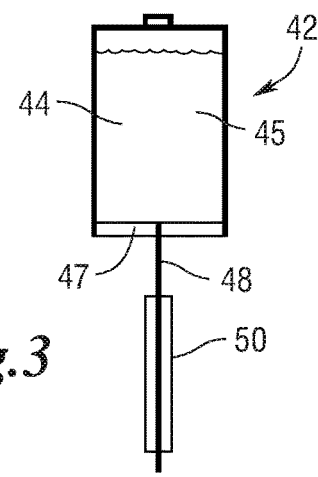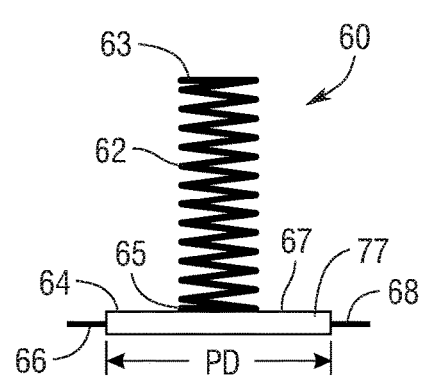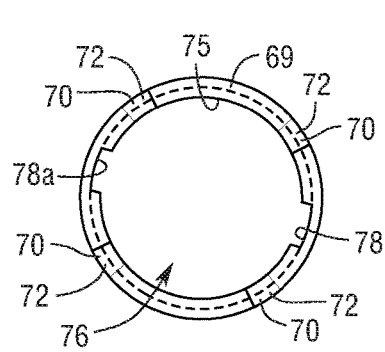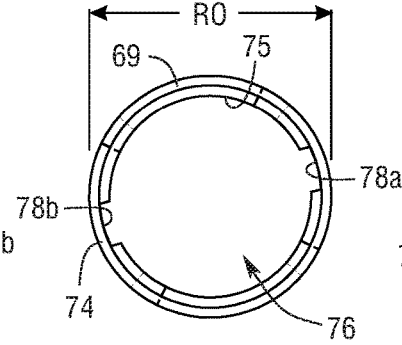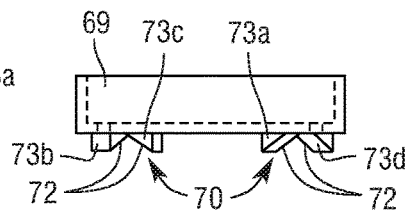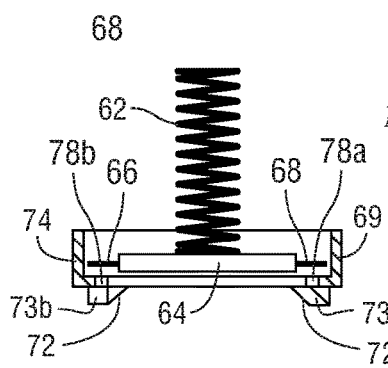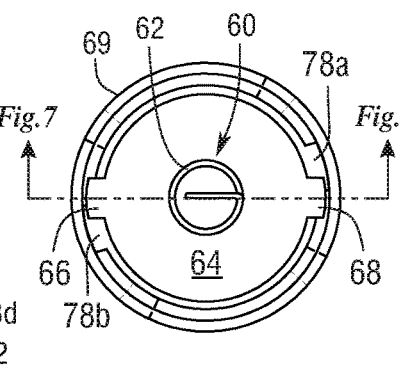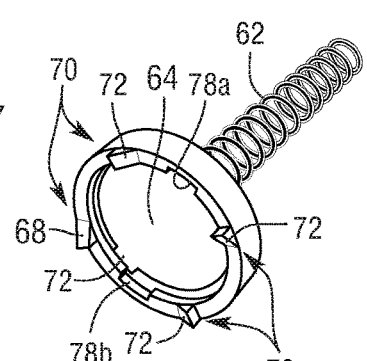

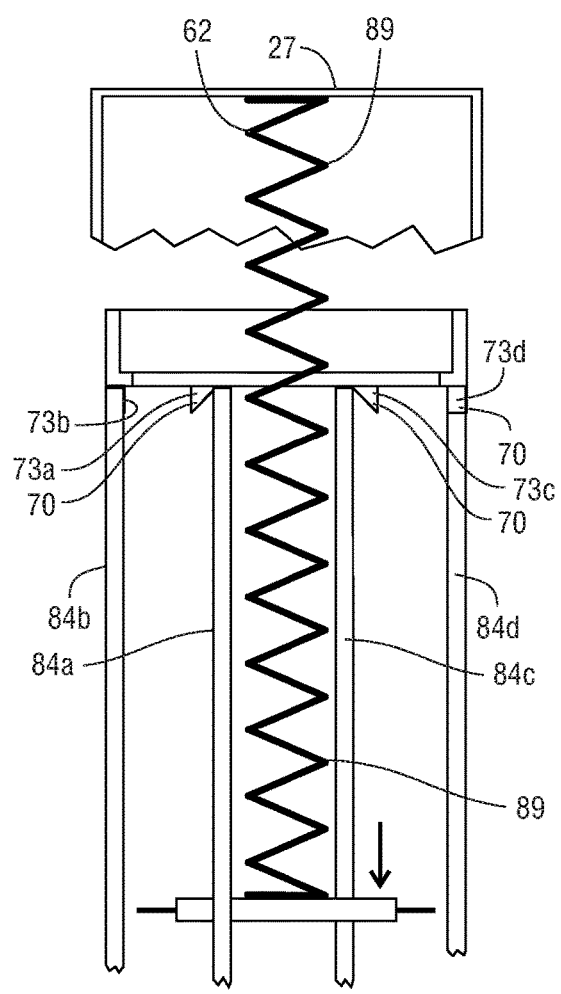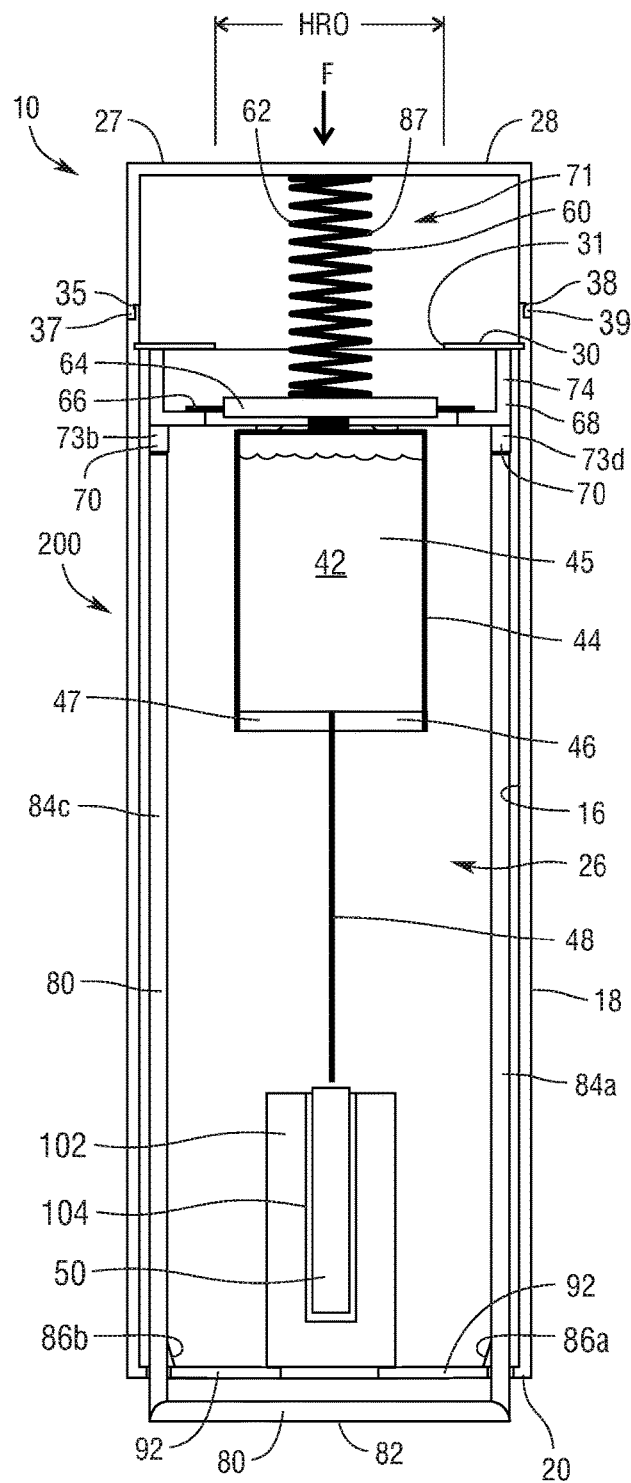
Fig.13
Fig.14

INJECTION DEVICE

This application claims the benefit of U.S. Provisional Patent Application having Application No. 62/422,206 filed on Nov. 15, 2016 the entire disclosure and contents of which are hereby incorporated herein by reference.

BACKGROUND

There are a great number of people who rely on drug delivery devices. One form or type of a drug delivery device is a hand held injection device that a person can use to inject himself or herself with medicine, or a person can use to inject a another person having a medical emergency with medicine. The hand held injection device holds medicine and has a needle for delivering the medicine to the patient. Hand held drug delivery devices are oftentimes used to administer life saving medicines in emergency situations.

When a person is having an allergic reaction the person needs immediate medicine to prevent the person from dying. For example, some people have a condition known as anaphylaxis, meaning they have serious allergic reactions when exposed to different trigger materials, for example foods, medicine, venom from a bee sting, and so on. One of the treatments for a person in anaphylaxis shock due to a severe allergic reaction is an injection of epinephrine into the leg of the person.

Currently there are delivery devices to capable of delivering epinephrine to the person having a medical emergency, however the current delivery devices are extremely expensive and typically cost $500 dollars or more for a single dose of epinephrine. The costs for current injection devices are even more burdensome, because they must be disposed of and replaced every year to ensure the epinephrine in the delivery device is always fresh and medically effective.

Thus, what is need is an injection device that is capable of delivering effective doses of medicine such as epinephrine, while at the same time is easy to use, is inexpensive, may be reused, and can be mass produced at a low production cost.

SUMMARY OF INVENTION

An injection device is provided having a housing. The housing has an end wall and the housing supports an access door that allows access to a housing interior. An end cap is mounted on the housing. The injection device also includes a cartridge assembly having a cartridge housing for holding a liquid to be dispensed, such as epinephrine, and the cartridge assembly is positioned internal to the housing. The cartridge assembly has a plunger that is positioned internal to the cartridge housing, and an injection needle extends from the plunger such that liquid to be dispensed is capable of exiting through the injection needle. A sterile sleeve is fitted over the injection needle to maintain a sterile environment for the injection needle. The cartridge assembly can be replaced by way of the access door or the injection device may be disposed or after use or after the liquid to be dispensed expires.

The injection device also includes a main spring assembly that includes a main spring that extends from a plate and first and second support arms extend from the plate. The main spring is positioned such that it abuts against the housing end wall and the plate.

The injection device also includes a release component that is positioned internal to the housing, and the release component has teeth that have sliding surfaces. The release component also has a release ring and the teeth extend from the release ring. The release ring defines a release ring opening and defines first and second release slots. The first and second release slots are sized such that first and second first and second support arms can slide through them when the release component is rotated into alignment with therewith.

The injection device also includes an actuator having an actuator ring from which first, second, third and fourth actuator rods extend and the actuator is also positioned internal to the housing. The first, second, third and fourth actuator arms are for engaging the release component to cause the release component to rotate and thus release the main spring. The first actuator rod has a first tab and the second actuator rod has a second tab. In other embodiments there may be more or less than four actuator rods. The injection device also has a stop wall, and the first, second, third and fourth actuator rods extend through the stop wall and the stop wall prevents components internal to the housing from completely exiting the housing.

When actuator ring is pressed against, for example, the leg of a person, the first, second, third and fourth actuator rods operatively engage the sliding surfaces of the teeth and the release component rotates. As this occurs, the first and second support arms that extend from the plate are moved into alignment with the first and second release slots defined in the release ring, and as soon as this occurs the main spring is released and expands. The plate impacts the cartridge housing and this causes the plunger to compress the fluid in the cartridge housing, and this results in the fluid flowing through the injection needle and into the leg of the person being injected.

The cartridge assembly can be replaced as needed or desired, for example after use or if the fluid or medicine in the cartridge housing expire due to its age.

BRIEF DESCRIPTION OF THE DRAWING FIGURES

FIG. 1 is front view of an injection device.
FIG. 2 is perspective view of the injection device.
FIG. 2A is bottom view a housing and showing the first end of the housing.
FIG. 2B is a front view of the housing.
FIG. 2C is a sectional view of the housing.
FIG. 3 is an exploded view of a cartridge assembly.
FIG. 4 is a front view of assembled cartridge assembly.
FIG. 5 is a side view of a main spring assembly.
FIG. 6 is a bottom view of a release component.
FIG. 6A is a top view of the release component.
FIG. 6B is a front view of the release component.
FIG. 7 is a front view of the main spring assembly abutting the release component.
FIG. 7A is a top view of the main spring assembly and release component shown in FIG. 7.
FIG. 8 is a perspective view of the main spring assembly abutting the release component.
FIG. 9 is a front view of an actuator.
FIG. 10 is a perspective view of the actuator.
FIG. 11 is a front view of the main spring assembly, the release component, and the actuator and the cartridge assembly is not shown for the sake of clarity.
FIG. 12 is front view of the main spring assembly, the release component, and the actuator as the release component rotates and releases the main spring assembly and the cartridge assembly is not shown for the sake of clarity.

FIG. 13 shows a front view of the main spring assembly after having been released from the release component and the cartridge assembly is not shown for the sake of clarity.

FIG. 14 is a sectional view of the injection device when in a compressed position.

DESCRIPTION

Figure 1:
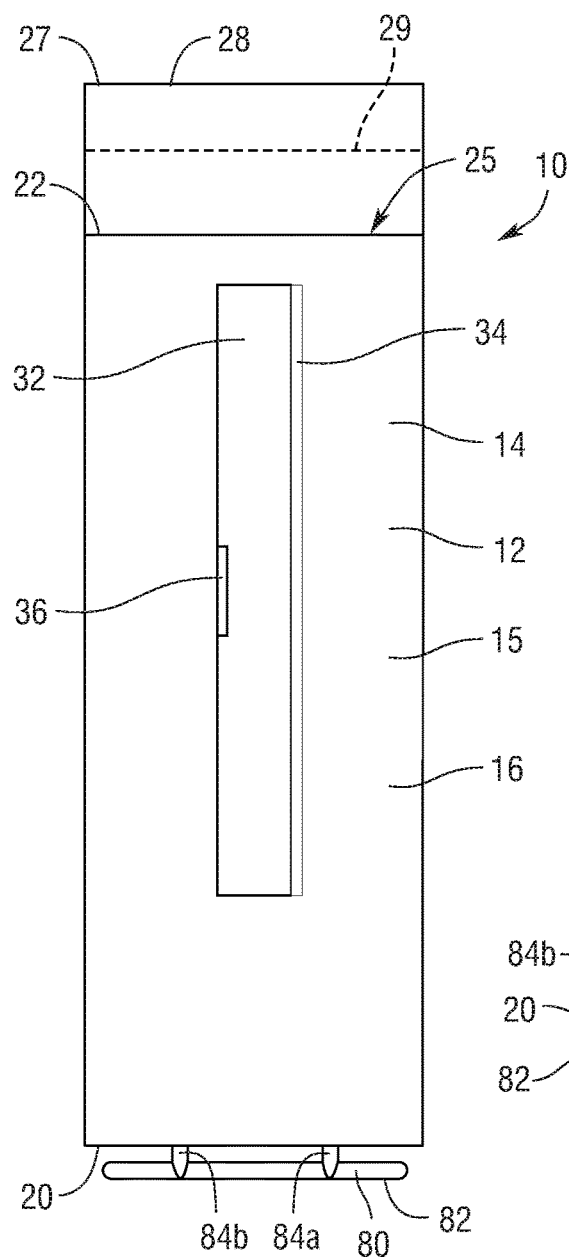
Figure 2:
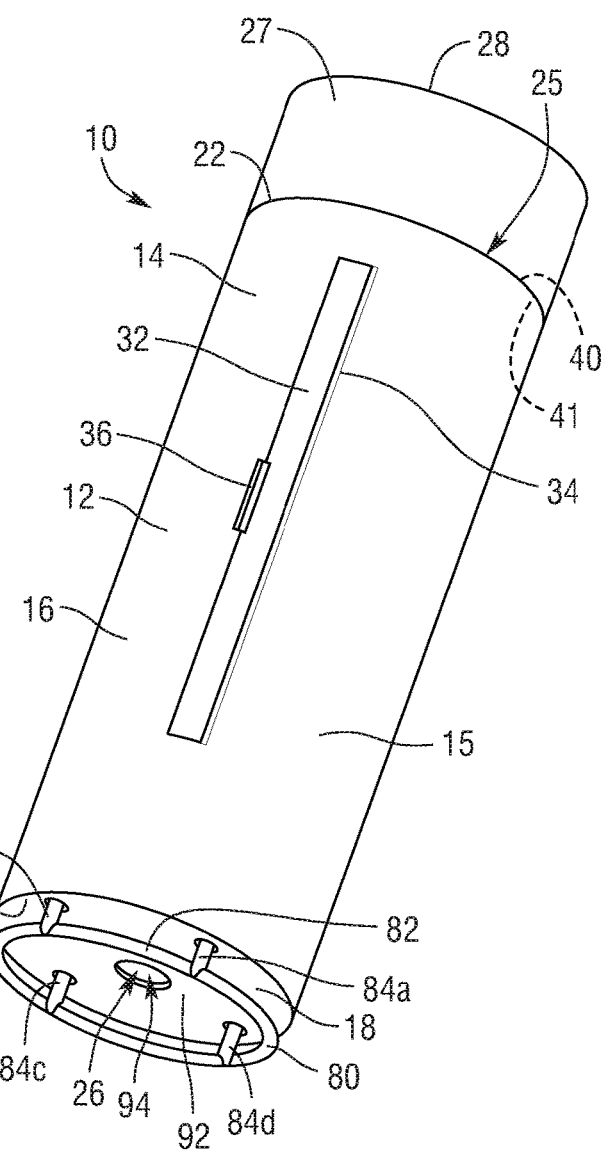
Figure 2A:
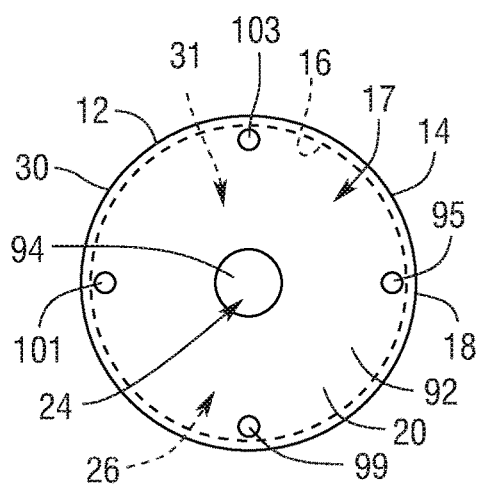
Figure 2C:
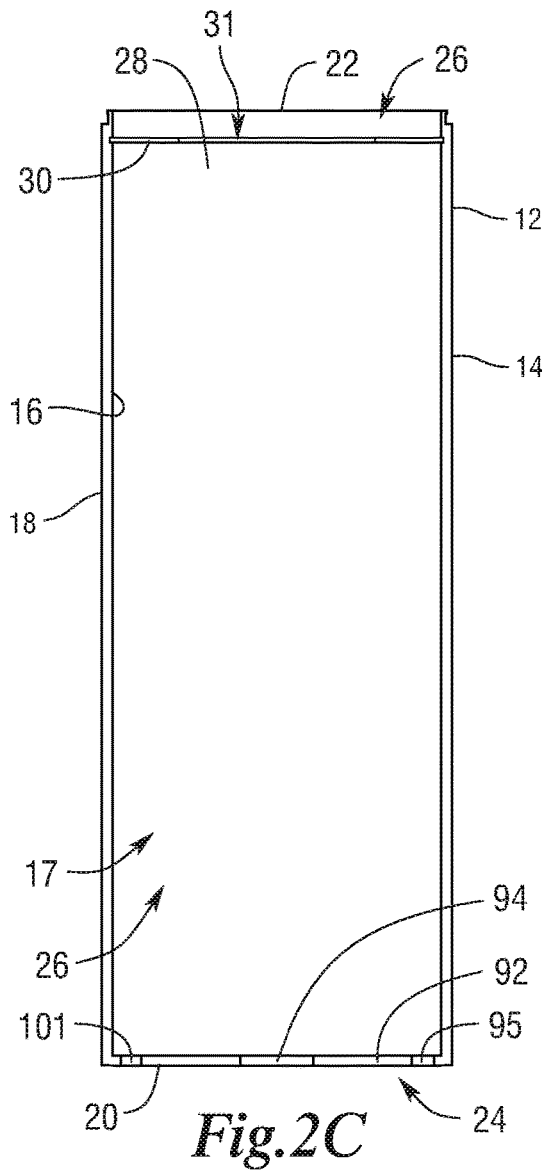
Figure 2B:
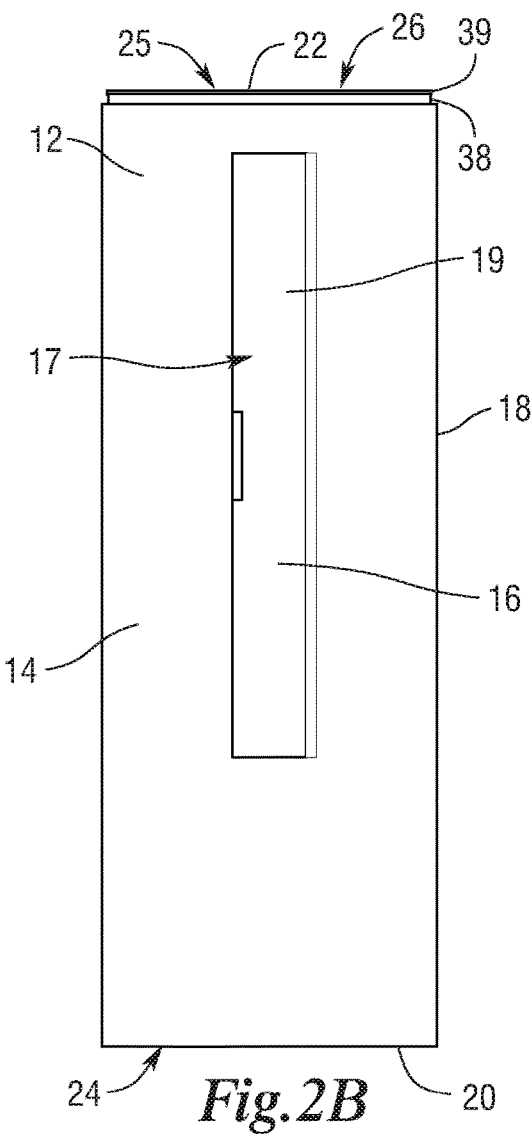
Figure 15:
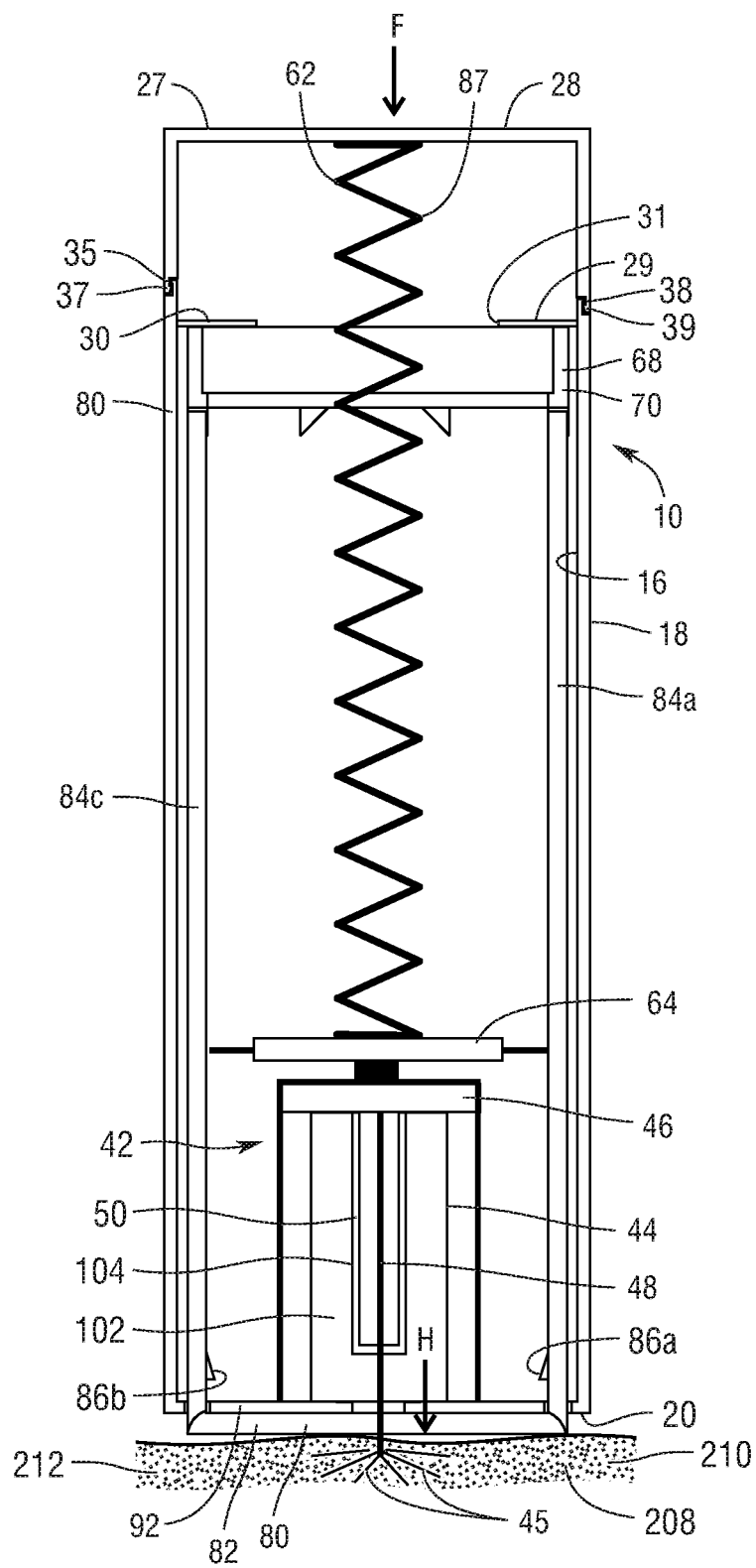
FIG. 15 is a sectional view of the injection device when in an expanded position.

As shown in FIGS. 1, 2, and 2A-2C, there is an injection device 10 that includes a housing 12, and the housing 12 has body portion 14 that has opposed first and second ends 20, 22, and the first end 20 defines a first opening 24, and the second end 22 defines a second opening 25. As shown the body portion 14 has a cylindrical shape 15, but it is to be understood that in other embodiments the body portion 14 could have a different geometry, for example it could be square shaped, or have some other geometry. The body portion 14 also has opposed interior and exterior body portion surfaces 16, 18. The housing 12 also includes an end cap 27 having an end wall 28 that mounted on the second end 22 of the body portion 14. The end cap 27 can be fitted on the body portion 14 with an interference fit or snap fit. As shown in FIG. 15, the end cap 27 defines an annular end cap recess 35, and the end cap has an end cap engagement lug 37 that defines a portion of the annular end cap recess 35 and the end cap engagement lug 37 extends into the annular end cap recess 35. Similarly, as shown in FIGS. 2B and 15, the second end 22 of the body portion 12 defines an annular body portion recess 38, and the body portion 12 has an annular body portion engagement lug 39 that defines a portion of the annular body portion recess 38 and the annular body portion lug 39 extends into the annular body portion recess 38. The end cap 27 can thus be snap-fitted on the body portion 12 by forcing the annular cap engagement lug 37 over the annular body portion engagement lug 39, such that the annular cap engagement lug 37 is positioned in the annular body portion recess 38, and the annular body portion engagement lug 39 is positioned in the annular end cap recess 35. Snap fitting components together is well known to those having ordinary skill in the art and there is not described in greater detail herein. In other embodiments the end cap 27 may be secured to the body portion 14 with a weld 40, or adhesives 41, or the end cap 27 may be threaded to the body portion 14. In another embodiment the end cap 27 may be replaced with a plug 29 (indicated by dashed line in FIG. 1) that can be inserted and removed from the second opening 25 defined in the second end 22 of the housing 12 and that is held in place with a friction fit or interference fit. In another embodiment the end cap 27 is secured with a weld 40 or adhesives 41. In another embodiment the end cap 27 is absent and the end wall 28 is connected to the second end 22 of the body portion 14 with a weld, adhesives, or an interference fit. Together the body portion 14 and the end cap 27 define a housing interior 26 and the first opening 24 leads to the housing interior 26.

The body portion 14 of the housing 12 also defines an access opening 19 that leads to the housing interior 26 as show in FIG. 2B. As shown in FIG. 1, there is an access door 32 mounted on the body portion 14 with hinges 34 so that a user can gain access to the housing interior 26 through the access opening 19. The access door 32 can be opened and closed by way of a latch 36 that may also serve as a handle. Latches for use in connection with doors are well know to those having ordinary skill in the art and are therefore not described in greater detail herein.

As best shown in FIGS. 2C, 14 and 15, the housing 12 further includes a housing ring 30 is supported by and extends from the interior surface 16 of the housing 12. The housing ring 30 defines a housing ring opening 31 having a housing ring opening diameter designated HRO in FIG. 14. As shown in FIGS. 1 and 2 an actuator ring 82 portion of an actuator 80 extends from the first end 20 of the housing 12 as will be described presently. The housing 12 also supports a stop wall 92 that extends from the interior surface 16 of the housing 12 as shown in FIGS. 2A, 14 and 15. The housing 12 may be made of plastic, metal, and other suitable materials.

As shown in FIGS. 3 and 4 the injection device 10 also has a cartridge assembly 42 having a cartridge housing 44 for holding a liquid 45 to be dispensed, for example medicine such as allergic reaction medicine, epinephrine, insulin, or other liquid that is not medicine, for example vitamins in a fluid form. The cartridge assembly 42 has a plunger 46 with a plunger head 47, and an injection needle 48 extends from the plunger head 47. Liquid 45 to be dispensed is capable of flowing through and exiting out of the injection needle 48. A sterile sleeve 50 is provided and it fitted over the injection needle 48 such that the injection needle 48 is kept sterile and is not exposed to the surrounding environment. As shown in FIGS. 14 and 15 the stop wall 92 supports a plunger stop block 102 that is positioned in the housing interior 26. The plunger stop block 102 defines a block needle opening 104 that is sized to receive the sterile sleeve 50, and the injection needle 48 is capable of piercing the sterile sleeve 50. As will be described presently, the plunger 46 impacts the plunger stop block 102 when the injection device 10 is triggered, and this causes the liquid 45 to flow through the injection needle 48.

Figure 12:
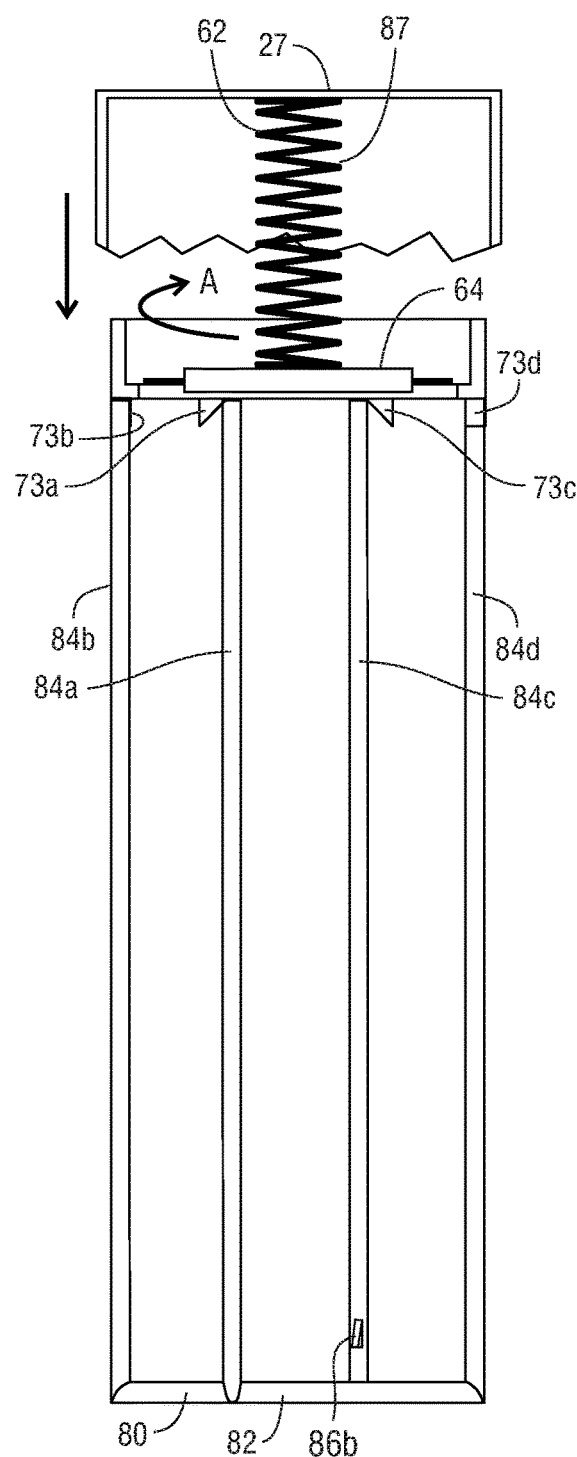

As shown in FIG. 5 the injection device 10 also has a main spring assembly 60. The main spring assembly includes a main spring 62 and a plate 64, and the plate 64 has a mounting surface 67. The main spring 62 is mounted on and extends from the mounting surface 67 of the plate 64. The plate 64 is cylindrical shaped as shown in FIGS. 7 and 7A, and the plate has a cylindrical surface 77 that meets with the mounting surface 67. The plate 64 has a plate diameter designated PD in FIG. 5. In one embodiment the plate diameter PD is greater than the housing ring opening diameter designated HRO. The main spring assembly 60 also includes first and second support arms 66, 68 that are mounted on and extend from the cylindrical surface 77 of the plate 64. The first and second support arms 66, 68 extend in opposite directions relative to one another, that is, they are mounted so as to be offset one hundred eighty degrees from one another relative to the cylindrical surface 77 of the plate 64. The main spring 62 has opposed first and second main spring ends 63, 65 and the first main spring end 63 is connected to the end wall 28 of the housing 12, and the second main spring end 65 is connected to the plate 64. The connections may be made with adhesives or a weld. As shown in FIGS. 14 and 15 the main spring 62 is positioned in the housing interior 26 and abuts against the above-described end wall 28 and the mounting surface 67 of the plate 64. FIGS. 12 and 14 shows the main spring 62 in a main spring compressed position 87, and FIG. 13 shows the main spring 62 as it expands, and FIG. 15 shows the main spring 62 in a main spring extended position 89. As shown in FIG. 14, the cartridge assembly 42 is mounted on the plate 64 or adhered to the plate 64 with an adhesive 41 so that the cartridge assembly 42 and the plate 64 are capable of moving together.

As shown in FIGS. 6-6B the injection device 10 also has a release component 69. The release component 69 has a release ring 74 and teeth 70, and the teeth 70 extend from the release ring 74. The teeth 70 have sliding surfaces commonly designated by reference numeral 72. In one embodiment shown in FIGS. 6B, 7 and 7A the teeth 70 include a first tooth 73a, a second tooth 73b, a third tooth 73c and a fourth tooth 73d each having a sliding surface 72. As shown in FIG. 6, the release ring 74 has a release ring interior surface 75 that defines a release ring opening 76 in the release component 69. The release ring interior surface 75 defines first and second release slots 78a and 78b, and the first and second release slots 78a, 78b are spaced one hundred eighty degrees from one another such that the first and second release slots 78a, 78b face one another. The first and second release slots 78a, 78b are sized and spaced from one anther such that the first and second support arms 66, 68, respectively, can slide or move through first and second release slots 78a, 78b, respectively, when the first and second support arms 66, 68 are moved into alignment with the first and second release slots 78a, 78b. The release ring opening 76 has in internal diameter designated RO in FIG. 6A. In addition, the internal diameter RO of the release ring 74 greater than the plate diameter PD such that the plate 64 can pass through the release ring 74. The above described housing ring opening diameter HRO 31 defined in the housing ring 30 is less than the plate diameter PD such that the plate 64 is unable to pass through the housing ring opening 31. As shown in FIG. 14 the release ring 74 abuts against the housing ring 30 such that the teeth 70 extend in a direction toward the first end 20 of the housing 12. FIGS. 7 and 8 show the main spring assembly 60 abutting the release component 69, and FIG. 7A is a top plan view showing the first and second support arms 66, 68 abutting the release component 69 and showing a the plate 64 spaced from the release component 69.

Figure 9:
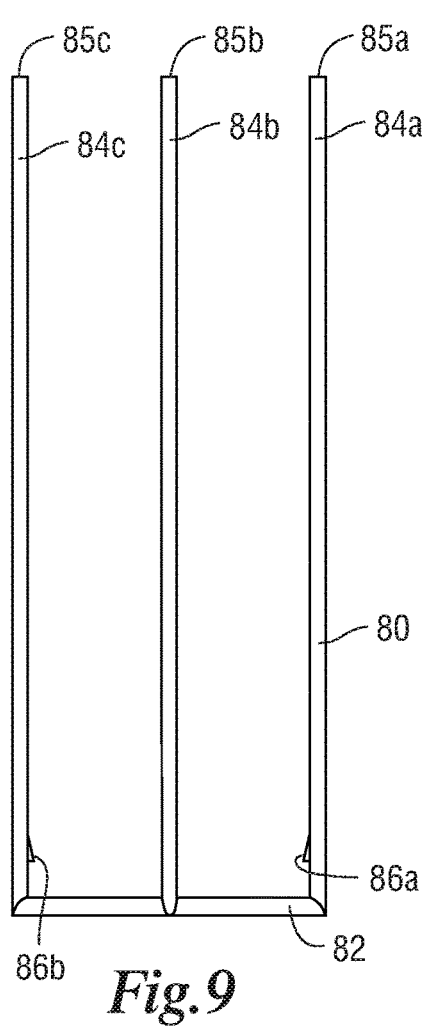
Figure 10:
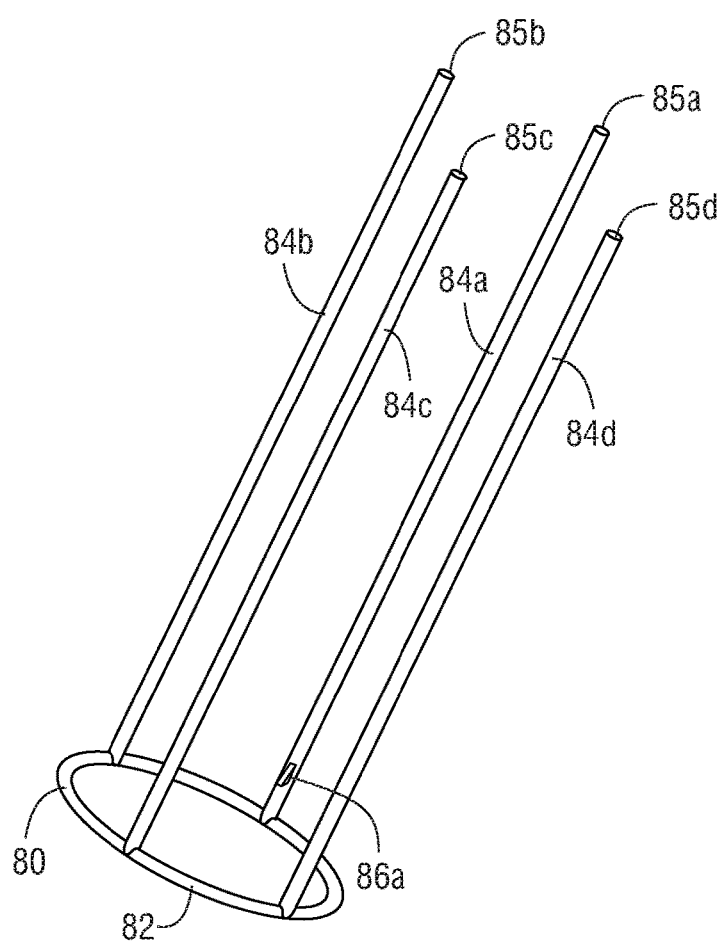

The injection device 10 also has an actuator 80 as shown in FIGS. 9 and 10. The actuator 80 has an actuator ring 82 from which extend first, second, third and fourth actuator rods 84a, 84b, 84c and 84d, respectively. The first actuator rod 84a has an first engagement end 85a, the second actuator rod 84b has a second engagement end 85b, the third actuator rod 84c has a third engagement end 85c and the fourth engagement rod 84d has a fourth engagement end 85d. In other embodiments there may just be the first actuator rod 84a, or just the first and second actuator rods 84a, 84b, or just the first second and third actuator rods 84a, 84b, 84c. In other embodiments there are more than four actuator rods. The first, second, third and fourth actuator rods 84a, 84b, 84c and 84d pass through the stop wall 92 as shown in FIG. 2. A first tab 86a extends from the first actuator rod 84a and a second tab 86b extends from the third actuator rod 84c. In another embodiment there is only the first tab 86a and the second tab 86b is absent, and in other embodiments all of the actuator rods may have tabs.

The stop wall 92 defines a central opening 94 that allows for the passage of the injection needle 48, and defines first, second, third and fourth actuator rod openings 95, 99, 101, 103 through which the first, second, third and fourth actuator rods 84a, 84b, 84c and 84d extend. The stop wall 92 is mounted to the interior surface 16 of the housing as shown in FIG. 2A and FIGS. 14 and 15, and the stop wall 92 may be held in place with a weld, or a friction fit or with adhesives. The stop wall 92 prevents the cartridge assembly 42 from completely exiting the housing 12. As shown in FIG. 14 the first and second tabs 86a, 86b abut against the stop wall 92 and this provides for only limited movement of the actuator 80, and prevents the actuator 80 from sliding too far out of the housing 12.

Figure 11:
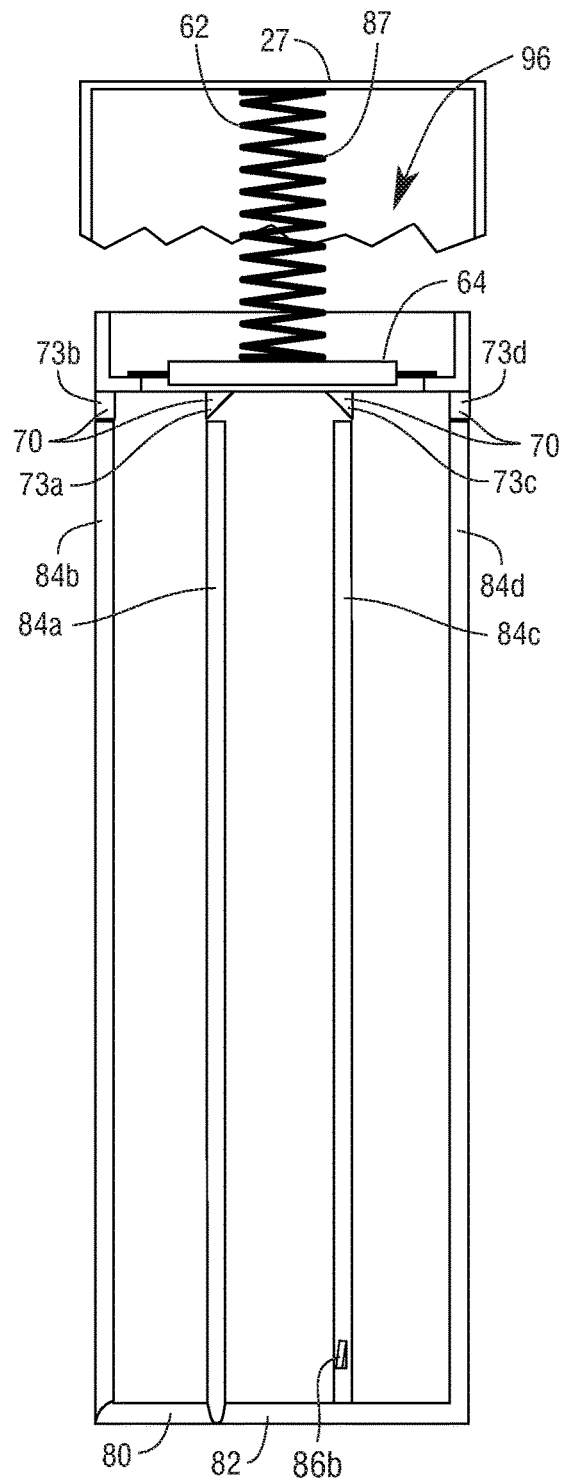

Turning now to FIGS. 11-13, there is shown the operative relationship between the actuator 80, the release component 69, and the plate 64. It is pointed out that for the sake of clarity the only a portion of the housing 12 and actuator 80 are shown, and the cartridge assembly 42 is not shown in FIGS. 11-13. In FIG. 11, the main spring 62 is in the main spring compressed position 87, and at this point the injection device 10 is in a cocked position 96. As shown in FIG. 11, the first, second, third and fourth engagement ends 85a, 85b, 85c, and 85d of the first, second, third and fourth engagement rods 84a, 84b, 84c and 84d contact the sliding surfaces 72 of the teeth 70, and more particularly along the sliding surfaces 72 of the first tooth 73a, second tooth 73b, third tooth 73c and the fourth tooth 73d. As show in FIG. 14, the first and second tabs 86a, 86b abut the stop wall 92 such that the first, second, third and fourth actuator rods 84a, 84b, 84c and 84d abut the teeth 70.

In use, and as shown in FIGS. 11-14 a person 210 grasps the housing 12 of injection device 10. The person 210 may be a medic, a third party or may be the actual end user that is self-administering the injection. The person 210 moves the actuator ring 82 into contact with a surface 206, for example the skin 208, as shown in FIG. 15. Next, he or she applies force designated F, for example, a hand generated force F to the end wall 28, or he or she holds and pushes on the housing 12 such that the actuator ring 82 is pushed into the skin 208. This causes the first, second, third and fourth actuator rods 84a, 84b, 84c and 84d to move into the housing 12 and rotate the release component 69. As shown in FIG. 15 the first second tabs 76a, 76b move away from the stop wall 92. When the first and second release slots 78a, 78b align with the first and second support arms 66, 68 the main spring 62 is released and moves from the main spring compressed position 87 to the main spring extended position 89. In other words, as the actuator ring 80 is pressed against the skin 208 the first second third and fourth engagement ends 85a, 85b, 85c, and 85d of the first second third and fourth actuator rods 84a, 84b, 84c, 84d slide along the sliding surfaces 72 of the first tooth 73a, a second tooth 73b, a third tooth 73c and a fourth tooth 73d. This forces the release component 69 to rotate as indicated by the arrow designated A in FIG. 12. As this occurs and as the release component 69 rotates the first and second release slots 78a, 78b move into alignment with the first and second support arms 66, 68. The moment the alignment is achieved the main spring 62 is released and immediately expands and forces or moves the plate 64 through the ring opening 76 defined in the release ring 74. The plate 64 moves through the actuator 80, that is the plate 64 moves past the first, second, third and fourth engagement rods 84a, 84b, 84c and 84d, and the plate 64 also moves the cartridge housing 44 when the main spring 62 is released.

As shown in FIGS. 13 and 15, as the main spring 62 continues to expand and move the cartridge housing 44 through the housing 12. As movement continues the plunger head 47 eventually impacts the plunger stop block 102 and the injection needle 48 pierces sterile sleeve 50 and the skin 208 of the person 210. As the main spring 62 continues to expand the plunger head 47 moves or slides deeper into the cartridge housing 44 due to impact with the plunger stop block 102, and the pressure on the liquid 45 in the cartridge housing 44 increases thus causing the liquid 45 to flow into the injection needle 48. As expansion of the main spring 62 continues all of the liquid 45 is forced out of the cartridge housing 44 and through the injection needle 48 and into the person 210 as shown in FIG. 15. Then, when the injection process is completed and the pressure on the actuator ring 80 is removed, the injection device 10 is lifted off the skin 208.

The injection device 10 can be reused. After the injection device 10 has been used in the manner described above (or the liquid therein has expired) a new cartridge assembly 42 can be installed in the housing 12. There are at least two scenarios wherein the cartridge assembly 42 can be or needs to be replaced.

The first scenario is when the injection device 10 has been used to deliver an injection of fluid 45, for example medicine, to a person as described above. After the injection device 10 has been used, the access door 32 is opened and the spent cartridge assembly 42 needs to be removed. The person 210 has to first reset the main spring 62 by manually pressing it back up into the housing 12 turning or rotating the plate 64 such the first and second support arms 66, 68 abut and are supported on the release component 69. The main spring 62 is then in the main spring compressed position 87. This step frees the used cartridge assembly 42 and allows the user to manually extract the used cartridge assembly 42 from the housing 12. When placing the new cartridge assembly 62 into the housing 12, the sterile sleeve 50, which is rectangular shaped in one of the preferred embodiments, assist in aligning the cartridge assembly 42 and thus holding it in place.

In the second scenario an expired cartridge assembly 42 needs to be replaced for example when the fluid 45, for example medicine, contained therein is has expired and is no longer useful. To replace an expired cartridge assembly 42 the same steps described immediately above are followed, but there is no need to manually compress the main spring 62 because it is already in a compressed state. The sterile sleeve 50 provides for alignment such that the cartridge assembly 42 is installed properly when the carriage assembly 42 is replaced.

In another embodiment the injection device 10 is disposed of after use or when the fluid 45, for example medicine, has expired.

In another embodiment there is only the first support arm 66 and there is only the first release slot 78a, and in other embodiments there are more than two support arms and more than two release slots.

It will be appreciated by those skilled in the art that while the injection device 10 has been described in detail herein, the invention is not necessarily so limited and other examples, embodiments, uses, modifications, and departures from the embodiments, examples, uses, and modifications may be made without departing from the injection device 10. All these embodiments are intended to be within the scope and spirit of the appended claims.

What is claimed:

1. An injection device comprising:
   a housing having a body portion with opposed first and second ends and the first end defines a first opening and the second end defines a second opening, and the housing has opposed interior and exterior body portion surfaces, and the housing includes an end cap having an end wall that mounted on the second end of the body portion and the body portion and the end cap define a housing interior;
   a main spring assembly having a main spring and a plate and the main spring is connected to the plate and the end wall, and first and second support arms extend from the plate;
   a release component having a release ring and a tooth, and wherein the tooth extends from the release ring and the tooth has a sliding surface and the release ring defines first and second release slots that are sized such that the first and second support arms are capable of sliding through the first and second release slots and wherein the first and second support arms abut against the release ring;
   an actuator having an actuator ring and having a first actuator rod with a first engagement end, and the first actuator rod extends from the actuator ring and the actuator is fitted in the housing such that the first engagement end of the actuator rod abuts against the tooth and wherein the first engagement end is capable of sliding along the sliding surface of the tooth;
   a cartridge assembly having a cartridge housing and the cartridge assembly having a plunger with a plunger head and an injection needle that extends from the plunger head and the plunger head is fitted in the cartridge housing and the cartridge housing is fitted in the housing and fixed to the plate;
   a stop wall mounted to the housing body portion surface and the stop wall supports a plunger stop block and the plunger stop block defines a block needle opening and the stop wall defines a central opening that allows for the passage of the injection needle and defines a first actuator rod opening through which the first actuator rod can pass; and,
   wherein when the actuator ring is pressed against a surface the first actuator rod engages the sliding surface of the tooth causing the release component and tooth to rotate such that as rotation of the release component continues the first and second release slots rotate into alignment with the first and second support arms, and upon alignment the main spring is be released and forces the plate and cartridge assembly through the housing such that the plunger head impacts and presses against the plunger stop block causing a fluid in the cartridge housing to flow out of the carriage housing, through the injection needle and out of the injection needle.

2. The injection device according to claim 1 wherein the housing also includes a housing ring that defines a housing ring opening and the housing ring is mounted on the interior body portion surface and the housing ring is positioned between the end wall and the actuator and wherein the plate is unable to pass through the housing ring opening.

3. The injection device according to claim 2 wherein the main spring is movable from a main spring compressed position to a main spring expanded position when the main spring is released.

4. The injection device according to claim 1 wherein the housing defines an access opening and an access door mounted on the body portion with hinges in order to allow for access to the housing interior.

5. The injection device according to claim 4 wherein the cartridge assembly can be removed through the access opening and another cartridge assembly can be installing in the housing through the access opening.

6. The injection device according to claim 1 wherein the actuator ring further includes second, third and fourth actuator rods and the release component has release teeth that are capable of engaging the second, third and fourth actuator rods so as cause the rotation of the release component.

7. The injection device according to claim 1 wherein the first actuator rod has a first tab and wherein the first tab is disposed internal to the housing and abuts the stop wall such that the movement of the actuator is limited.

8. An injection device comprising:
a housing having a body portion and an end cap;
a main spring assembly having a main spring and a plate and the main spring is connected to the plate and the main spring abuts against the end cap and the plate, and first and second support arms are extend from the plate;
a release component having a release ring and a tooth and wherein the release component defines first and second release slots that are sized such that the first and second support arms are capable of sliding through the first and second release slots and wherein the first and second support arms abut against the release ring;
an actuator having an actuator ring and having a first actuator rod with a first engagement end, and the first actuator rod extends from the actuator ring and the actuator is fitted in the housing such that the first engagement end of the actuator rod abuts against the tooth and wherein the first engagement end is capable of sliding along the sliding surface of the tooth;
a cartridge assembly having a cartridge housing and the cartridge assembly having a plunger with a plunger head and an injection needle that extends from the plunger head and the plunger head is fitted in the cartridge housing;
a stop wall extends from the interior body portion surface and the stop wall supports a plunger stop block and the plunger stop block defines a block needle opening the stop wall defines a first actuator opening and the first actuator rod extends through the first actuator opening and the stop wall defines a central opening to allow the passage of the injection needle; and,
wherein when the actuator ring is pressed against skin the first actuator rod engages the sliding surface of the tooth causing the tooth and the release component to rotate such that as rotation of the release component continues the first and second release slots rotate into alignment with the first and second support arms causing the main spring to be released, and the mainspring forces on the plate to move the plate and cartridge housing through the housing causing the plunger head to press against the plunger stop block to cause a fluid in the cartridge housing to flow out of the cartridge housing and out of the injection needle.

9. A method of making an injection device comprising the acts of:
providing a housing and providing the housing with a body portion with opposed first and second ends and defining first and second openings in the first and second ends and providing the housing with an end cap;
defining a housing interior in the housing;
providing a main spring assembly having a main spring and a plate and connecting the main spring to the plate and the main spring abuts against the end cap, and extending first and second support arms from the plate;
providing a release component with a release ring and a tooth, and wherein the tooth extends from the release ring and the tooth has a sliding surface, and defining first and second release slots in the release component that are sized such that the first and second support arms are capable of sliding through the first and second release slots and wherein the first and second support arms abut against the release ring;
providing an actuator having an actuator ring and extending a first actuator rod with a first engagement end from the actuator ring, and fitting the actuator in the housing such that the first engagement end of the actuator rod abuts against the tooth and wherein the first engagement end is capable of sliding along the sliding surface of the tooth;
providing a cartridge assembly having a cartridge housing and positioning a plunger head in the cartridge housing and providing an injection needle and extending the injection needle from the plunger head and placing the carriage assembly in the housing;
mounting a stop wall in the housing interior and mounting a plunger stop block on the stop wall and the plunger stop block defines a block needle opening, and defining a central opening and a first actuator opening in the stop wall, and the first actuator rod extends through the first actuator opening; and,
wherein when the actuator ring is pressed against a surface the first actuator rod engages the sliding surface of the tooth causing the release component and tooth to rotate such that as rotation of the release component continues the first and second release slots rotate into alignment with the first and second support arms and upon alignment the main spring is released, and the main spring forces on the plate to move the plate and the cartridge housing through the housing causing the plunger head to press against the plunger stop block such that a fluid in the cartridge housing flows out of the cartridge housing, through the injection needle, and out the injection needle.

10. The method of making an injection device according to claim 9 including the further acts of providing the housing with a housing ring that defines a housing ring opening and mounting the housing ring on the interior body portion surface and positioning the housing ring between the end wall and the actuator and wherein the plate is unable to pass through the housing ring opening.

11. The method of making an injection device according to claim 10 wherein upon pressing the actuator against the skin of a person the main spring is released and moves from a main spring compressed position to a main spring expanded position.

12. The method of making an injection device according to claim 9 including the further step of defining an access opening in the housing an providing an access door and mounting the access door on the housing.

13. The method of making an injection device according to claim 12 including the acts of sizing the access opening such that the cartridge assembly can be removed through the access opening and another cartridge assembly can be installing in the housing through the access opening.

14. The method of making an injection device according to claim 9 further comprising the acts of providing the actuator ring with second, third and fourth actuator rods and providing the release component with release teeth that are capable of engaging the second, third and fourth actuator rods so as cause the rotation of the release component.

* * * * *